March 24, 1964 R. S. MOORE Plant Pat. 2,384
ROSE
Filed Jan. 12, 1962
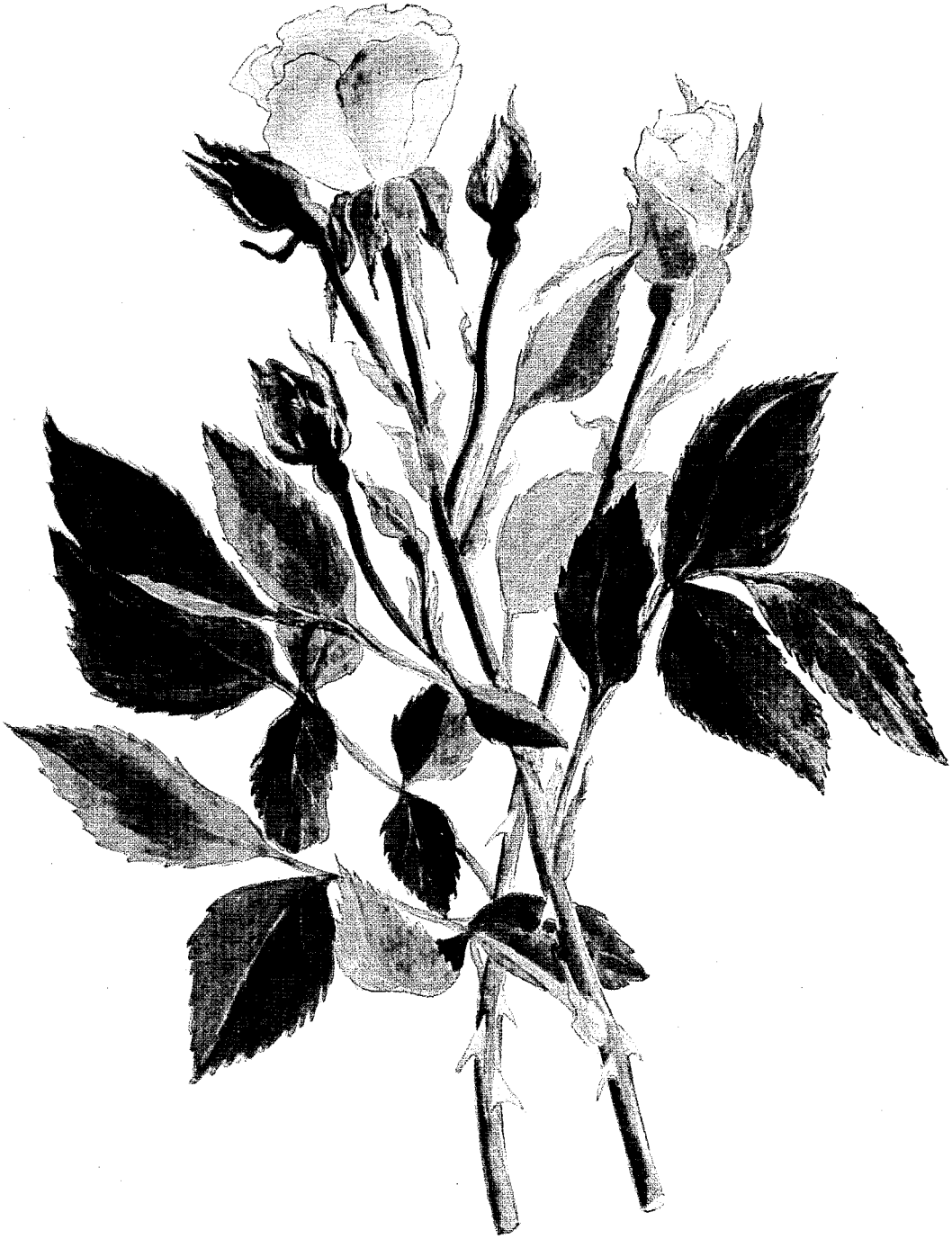
WITNESS
Jeanette Nunn Copley
INVENTOR
RALPH S. MOORE
ATTYS.
Eckhoff and Slick

United States Patent Office

Plant Pat. 2,384
Patented Mar. 24, 1964

2,384
ROSE

Ralph S. Moore, 2519 E. Mineral King, Visalia, Calif.

Filed Jan. 12, 1962, Ser. No. 165,975
1 Claim. (Cl. Plt.—6)

This invention relates to a new and distinct variety of tall, pillar-like climbing floribunda rose plant.

This plant is characterized as to novelty by its active growth, which resembles one of its grandparents, Wilhelm (Skyrocket), unpatented, and by its bright red color with an orange fluorescent undertone, which resembles Floradora, unpatented.

This new variety is a pillar-climber which continues to repeat bloom so long as growth is active and weather permits. Most of the shoots, even of the current season's growth, including the strong climbing shoots, terminate in flowers. Young plants tend to flower the first year they are planted.

This new variety of plant will bloom even if pruned into bush form. Bud form (shape) is hybrid tea. If a fully opened flower is held upside down, the petals flare out to resemble a ballerina's skirt.

This variety of climbing floribunda rose plant was originated by me, in my nursery located at Visalia, California, and under conditions of careful control and observation, by first crossing the variety Sister Therese (unpatented) with Wilhelm (Skyrocket); then from a selected seedling of this cross, 1600 seeds were planted (these were self-pollinated). From these 1600 seeds, plants grew and the new and distinct variety claimed herein was selected. Subsequent to origination of the variety, I successfully asexually reproduced it in my nursery, located as aforesaid, by budding as well as cuttings, the reproductions having run true in all respects.

The drawing illustrates the variety including foliage, buds and flowers.

Referring now specifically to the new and distinct variety of floribunda rose plant, the following is a detailed description thereof in outline; all major color plate identifications being to the British Colour Council Horticultural Colour Chart, except where common terms of color definition are employed.

Type: Half hardy to hardy; tall; pillar; outdoor; seedling; cut flowers; garden decoration.
Class: Climbing floribunda.

*Flowers*

Continuity: Intermittent to continuous.
Fragrance: Moderate to strong.
Flowers borne: From three to five or more, sometimes ten to twenty, arranged loosely on stem in irregular, rounded clusters; on normal, medium length stems.
Quantity of bloom: Abundant, outdoors.
Bud:
- *Peduncle.*—long; slender; medium erect; medium green; numerous short brown hairs.
- *Before calyx breaks.*—Size—medium. Form—pointed, oval, with a conspicuous neck, with foliaceous appendages on the surface of the bud, with foliaceous parts extending beyond the tip of the bud, equal to ¼ or more of its length. Color—green.
- *As calyx breaks.*—Color—bright red.
- *As first petal opens.*—Size—medium. Form—ovoid. Color: outside—Cardinal Red 822/1 with sometimes darker tones; inside—Blood Red 820/1 overlaid with Cardinal Red 822 (shade changes according to the light, like velvet). Opening—opens well at all times and in all weather.

Bloom:
- *Size when fully opened.*—Medium, 2⅛" to 2¾".

- *Petalage.*—Double; from 20 to 25 petals arranged regularly.
- *Form.*—Full and globular at first; becoming cupped and high centered; petals remaining at first loosely rolled outward; becoming later, at maturity, very loosely rolled outward. Petals are saddle-shaped.

Petals: Thick; leathery; inside shiny and satiny; outside satiny.
- *Shape.*—Outside—broad obovate; intermediate—obovate; inside—obovate. (Note: In spring, ends of many (if not all) petals are notched (or pinked) as though trimmed with pinking shears.)
- *Color.*—Newly opened flower from plant grown outdoors (September)—(1) Outside petal: outside surface—near white at base shading into Turkey Red 721/3; inside surface—base lighter, thence shading into Currant Red 821/3. (2) Intermediate petal: outside surface—Cherry 722/3; inside surface—near white at base shading to Currant Red 821/3. (3) Inner petal: outside surface—Cherry 722/3; inside surface—near white at base shading to Currant Red 821/3. Rose opened for three days outdoors (September)—Outside petal: outside surface—tip of white at base shading to Cherry 722/3 or lighter; inside surface—near white at base shading to Cherry 722/2. Inside petal: outside surface—near white tip at base shading into Tyrian Rose 24 or 24/1; inside surface—near white tip at base shading into Cherry 722/3.
- *General color effect.*—Newly opened flower—bright red with an orange fluorescent undertone. Flower open three days—bright rose or pink-red.
- *Behavior.*—Part drop off cleanly, some persist; fade to brown; color often brightest in warm weather although petals may sometimes burn in extreme hot weather.
- *Flower longevity.*—Three to five days on bush in garden (September). Two to four days as cut roses grown outdoors and kept at living room temperatures (September).

Reproductive organs:
- *Stamens.*—Of medium number; arranged regularly about pistils.
- *Filaments.*—Of medium length; reddish; most with anthers.
- *Anthers.*—Small to medium size; reddish; all open at once.
- *Pollen.*—Of moderate abundance; yellow.
- *Pistils.*—Of medium number.
- *Styles.*—Uneven; short to medium length; medium heavy; loosely bunched.
- *Stigma.*—White.
- *Ovaries.*—Enclosed in calyx.
- *Hips.*—None.
- *Sepals.*—Permanent; long; spear shaped, recurved; green becoming brown.
- *Seeds.*—None.

*Plant*

Foliage:
- *Leaves.*—Compound of 5 and sometimes 7 leaflets; of normal abundance; medium large; heavy; leathery; semi-glossy.
- *Leaflets.*—Lanceolate; apex—acute; margin—serrate.
- *Color.*—Mature: upper surface—normal green; under surface—normal green. Young: upper surface—normal green shaded to bronze or red on edges; under surface—normal green shaded to bronze or red on edges.
- *Rachis.*—Of medium weight; upper side grooved, hairy and prickly; under side sparsely prickly and thorny.
- *Stipules.*—Of medium length; moderately narrow;

with moderately short points turning out at an angle of more than 45°.

*Disease.*—Resistant to mildew as compared with other varieties grown under comparable cultural conditions at Visalia, California.

*Growth*

Habit: Bushy; upright; climbing; many branches.
Growth: Free vigorous.
Canes: Of medium weight.
Main stems: Gray to green.
*Thorns.*—Several; of medium length; hooked downward; with long, oval base.
*Prickles.*—Several to many.
*Hairs.*—None.
Branches: Green.
*Thorns.*—Several; of medium length; hooked downward; with long, round base.
*Prickles.*—Several; reddish.
*Hairs.*—None.
New shoots: Bright green.

*Thorns.*—Several; of medium length; hooked downward; with long narrow, round base.
*Prickles.*—Several; reddish.
*Hairs.*—Few.

The following is claimed:

A new and distinct variety of climbing floribunda rose plant, substantially as herein shown and described, of the tall, pillar, outdoor variety distinguished by its active growth and its bright red color, said active growth being characterized by most shoots terminating in flowers and young plants tending to flower in their first season, said growth habit resembling Wilhelm (Skyrocket), and said color being characterized by a bright red with an orange fluorescent undertone in newly opened flowers and bright rose or pink-red in flowers open for three days, said color resembling Floradora, said variety being capable of blooming even when pruned to bush form, flower buds being hybrid tea in shape, and with the blooms of the said variety arranged irregularly in loosely rounded clusters in a minimum quantity of three to five and a maximum quantity of twenty or more on each stem.

No references cited.